United States Patent [19]

Meyer et al.

[11] Patent Number: 4,562,210
[45] Date of Patent: Dec. 31, 1985

[54] BACTERICIDES

[75] Inventors: Willy Meyer, Riehen; Werner Töpfl, Dornach; Haukur Kristinsson, Bottmingen, all of Switzerland; Wolfgang Eckhardt, Lörrach, Fed. Rep. of Germany

[73] Assignee: Ciba-Geigy Corporation, Ardsley, N.Y.

[21] Appl. No.: 563,841

[22] Filed: Dec. 21, 1983

Related U.S. Application Data

[63] Continuation-in-part of Ser. No. 458,587, Jan. 17, 1983, Pat. No. 4,443,245, and a continuation-in-part of Ser. No. 458,696, Jan. 17, 1983, Pat. No. 4,425,154.

[51] Int. Cl.[4] .................. C07C 127/19; C07C 157/09
[52] U.S. Cl. ....................... 514/604; 564/42; 564/23
[58] Field of Search ............... 564/23, 42; 424/321

[56] References Cited

U.S. PATENT DOCUMENTS 3,420,882 1/1969 Muth et al. ............... 564/42
4,425,154 1/1984 Meyer et al. ............... 71/92

FOREIGN PATENT DOCUMENTS 1520220 4/1968 France .

Primary Examiner—Charles F. Warren
Assistant Examiner—R. A. Picard
Attorney, Agent, or Firm—Edward McC. Roberts

[57] ABSTRACT

Novel N-[2-(1,2-dichlorovinyloxy)phenylsulfonyl]-(thio)ureas of the general formula I

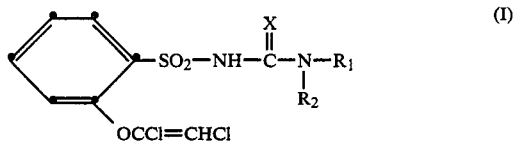

in which X is oxygen or sulfur, $R_1$ is hydrogen, $C_1$–$C_{12}$-alkyl, $C_2$–$C_6$-alkenyl or $C_2$–$C_6$-alkinyl; and $R_2$ is hydrogen, $C_1$–$C_{12}$-alkyl, $C_2$–$C_6$-alkenyl, $C_2$–$C_6$-alkinyl or $C_1$–$C_6$-alkoxy; and the salts of these compounds are described.

These compounds have pronounced bactericidal properties and can be used without problems against bacteria which damage plants, especially in the agricultural sector.

10 Claims, No Drawings

BACTERICIDES

CROSS REFERENCE TO RELATED APPLICATIONS

This application is a continuation-in-part of application Ser. Nos. 458,587 and 458,696, both filed Jan. 17, 1983, now U.S. Pat. Nos. 4,443,245 and 4,425,154, respectively.

The present invention relates to novel N-[2-(1,2-dichlorovinyloxy)-phenylsulfonyl]-(thio)ureas of the following formula I. It furthermore relates to the preparation of these substances and to agrochemical compositions containing at least one of these compounds as the active substance. The invention also relates to the use of the active substances or of the compositions for controlling harmful bacteria, especially phytopathogenic species.

The compounds according to the invention are those of the general formula I

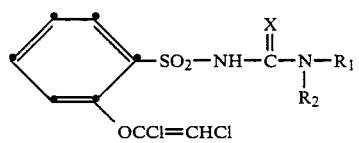

in which X is oxygen or sulfur; $R_1$ is hydrogen, $C_1$–$C_{12}$-alkyl, $C_2$–$C_6$-alkenyl or $C_2$–$C_6$-alkinyl; and $R_2$ is hydrogen, $C_1$–$C_{12}$-alkyl, $C_2$–$C_6$-alkenyl, $C_2$–$C_6$-alkinyl or $C_1$–$C_6$-alkoxy; and the salts of these compounds.

In the context of the formula I, the ureas are preferable to the thioureas.

The invention also relates to the salts which the compounds of the formula I can form with amines, alkali metal bases, alkaline earth metal bases or quaternary ammonium bases.

Of the alkali metal hydroxides and alkaline earth metal hydroxides as salt-forming agents, the hydroxides of lithium, sodium, potassium, magnesium or calcium, and especially those of sodium or potassium, are preferred.

Examples of amines which are suitable for salt formation are primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, in particular ethyl-, propyl-, diethyl- or triethyl-amine, and especially isopropylamine and diethanolamine. Tricyclic nitrogen bases, for example 1,4-diazabicyclo[2,2,2]octane, 1,8-diazabicyclo[5.4.0]undec-7-ene or 1,5-diazabicyclo[4.3.0]non-5-ene are also suitable.

Examples of quaternary ammonium bases are, in general, the cations of ammonium halide salts, for example the tetramethylammonium cation, the trimethylbenzylammonium cation, the triethylbenzylammonium cation, the tetraethylammonium cation and the trimethylethylammonium cation, and also the ammonium cation.

The term alkyl, by itself or as a constituent of another substituent, such as alkoxy and the like, is to be understood as meaning, for example, the following straight-chain or branched groups, depending on the number of carbon atoms stated: methyl, ethyl, propyl, butyl, pentyl, hexyl, heptyl, octyl, nonyl, decyl, undecyl, dodecyl and the like, and their isomers, for example isopropyl, isobutyl, tert.-butyl, isopentyl and the like. Alkenyl is, for example, prop-1-enyl, allyl, but-1-enyl, but-2-enyl or but-3-enyl, and chains with several double bonds. Alkinyl is, for example, prop-2-inyl, propargyl, but-1-inyl, but-2-inyl and the like, preferably propargyl.

The compounds of the formula I are oils, resins or, predominantly, crystalline solids at room temperature, which are distinguished by very useful bactericidal properties. They can be used, for example, preventively and curatively in the agriculture sector or related fields, for controlling phytopathogenic bacteria, in particular Xanthomonas species. The active substances of the formula I according to the invention have a high bactericidal activity and large action spectrum within a wide range of concentrations, and can be used without problems, especially in the agricultural sector.

The following groups of active substances are preferred because of their marked bactericidal activity, especially their phytobactericidal activity:

Group Ia: Compounds of the formula I in which X is oxygen or sulfur; $R_1$ is hydrogen or $C_1$–$C_6$-alkyl; and $R_2$ is hydrogen, $C_1$–$C_6$-alkyl, $C_2$–$C_6$-alkenyl, $C_2$–$C_6$-alkinyl or $C_1$–$C_6$-alkoxy.

Group Ib: Compounds of the formula I in which X is oxygen or sulfur; $R_1$ is hydrogen or $C_1$–$C_3$-alkyl; and $R_2$ is $C_1$–$C_6$-alkyl or $C_1$–$C_6$-alkoxy.

Group Ic: Compounds of the formula I in which X is oxygen; $R_1$ is hydrogen or $C_1$–$C_3$-alkyl; and $R_2$ is $C_1$–$C_6$-alkyl.

Other interesting sub-groups are:

Group Id: Compounds of the formula I in which X is oxygen or sulfur; $R_1$ is hydrogen or $C_1$–$C_3$-alkyl; and $R_2$ is $C_2$–$C_6$-alkenyl or $C_2$–$C_6$-alkinyl.

Group Ie: Compounds of the formula I in which X is oxygen; $R_1$ is hydrogen or $C_1$–$C_3$-alkyl; and $R_2$ is $C_2$–$C_4$-alkenyl or $C_2$–$C_4$-alkinyl.

Group If: Compounds of the formula I in which X is oxygen and $R_1$ and $R_2$ independently of one another are hydrogen, $C_2$–$C_6$-alkenyl or $C_2$–$C_6$-alkinyl.

Examples of specific particularly preferred substances are: N-[2-(1,2-dichlorovinyloxy)phenylsulfonyl]-urea (compound No. 1.1); N-[2-(1,2-dichlorovinyloxy)phenylsulfonyl]-N'-methylurea (compound No. 1.2); N-[2-(1,2-dichlorovinyloxy)phenylsulfonyl]-N'-isopropylurea (compound No. 1.5); N-[2-(1,2-dichlorovinyloxy)phenylsulfonyl]-N'-n-butylurea (compound No. 1.6); N-[2-(1,2-dichlorovinyloxy)-phenylsulfonyl]-N'-methoxy-N'-methylurea (compound No. 1.29); N-[2-(1,2-dichlorovinyloxy)phenylsulfonyl]-N'-allylurea (compound No. 1.20); N-[2-(1,2-dichlorovinyloxy)phenylsulfonyl]-N',N'-dimethylurea (compound No. 1.24); N-[2-(1,2-dichlorovinyloxy)-phenylsulfonyl]-N'-methyl-N'-ethylurea (compound No. 1.25); N-[2-(1,2-dichlorovinyloxy)phenylsulfonyl]-N'-methyl-N'-allylurea (compound No. 1.32); N-[2-(1,2-dichlorovinyloxy)phenylsulfonyl]-N'-methylthiourea (compound No. 2.2); N-[2-(1,2-dichlorovinyloxy)-phenylsulfonyl]-N'-isopropylthiourea (compound No. 2.5) and N-[2-(1,2-dichlorovinyloxy)phenylsulfonyl]-N'-allylthiourea (compound No. 2.20).

The preparation according to the invention of the compounds of the formula I is carried out in an organic solvent which is inert in the reaction, by (a) reacting a 2-(1,2-dichlorovinyloxy)phenylsulfonyl iso(thio)cyanate of the formula II

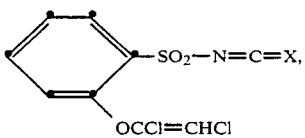 (II)

with an amine of the formula III

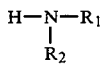 (III)

preferably in the presence of a base, or (b) reacting 2-(1,2-dichlorovinyloxy)phenylsulfonamide of the formula IV

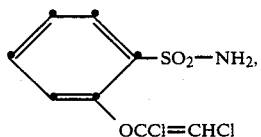 (IV)

with a carbamoyl halide of the formula

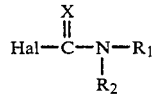 (V)

in the presence of a base; or (c) for the preparation of compounds of the formula I in which $R_1$ is hydrogen, by reacting 2-(1,2-dichlorovinyloxy)phenylsulfonamide of the above formula IV with an iso(thio)cyanate of the formula VI

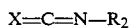 (VI)

in the presence of a base; the substituents $R_1$, $R_2$ and X are as defined under formula I and Hal is halogen, preferably chlorine or bromine and in particular chlorine.

If desired, the resulting ureas of the formula I can be converted into salts by means of amines, alkali metalhydroxides, alkaline earth metal hydroxides or quaternary ammonium bases. This is effected, for example, by reaction with the equimolar amount of base and evaporation of the solvent.

The compounds of the formulae III and VI are generally known, or they can be prepared by methods which are known per se.

The compounds of the formulae II and IV and their preparation are described in European Offenlegungsschrift EP No. 44,807.

Reactions a, b and c to give compounds of the formula I are advantageously carried out in aprotic inert organic solvents or solvent mixtures. Examples of suitable solvents or diluents are: aliphatic and aromatic hydrocarbons, such as benzene, toluene, the xylenes and petroleum ether; halogenated hydrocarbons such as chlorobenzene, methylene chloride, ethylene chloride, chloroform, carbon tetrachloride and tetrachloroethylene; ethers and ether-like compounds, such as dialkyl ethers (diethyl ether, diisopropyl ether, tert.-butyl methyl ether and the like), ethylene glycol dimethyl ether, diethylene glycol dimethyl ether, anisole, dioxane or tetrahydrofuran; nitriles such as acetonitrile or propionitrile; in some cases N,N-alkylated amides, such as dimethylformamide; dimethylsulfoxide; ketones, such as acetone, diethyl ketone and methyl ethyl ketone; and mixtures of these solvents with one another. In some cases, the reagent itself can serve as the solvent.

The reaction temperatures are in general between $-20°$ and $+120°$ C., preferably between 0° and $+30°$ C. The reactions in general proceed slightly exothermically and can be carried out at room temperature. The reaction mixture is appropriately heated to its boiling point for a short time for the purpose of shortening the reaction time or to start up the reaction. The reaction times can also be shortened by adding one drop of base as a reaction catalyst.

Bases which can be used are either organic bases, such as amines, for example tertiary amines (such as triethylamine, trimethylamine, tripropylamine, N-methylpiperidine, 1,4-diazabicyclo[2,2,2]octane, 1,8-diazabicyclo[5.4.0]undec-7-ene, and the like), pyridine and pyridine bases (such as 4-dimethylaminopyridine, 4-pyrrolidylaminopyridine, the picolines, lutidine and the like), and inorganic bases, such as hydrides, such as sodium hydride or calcium hydride, hydroxides, such as sodium hydroxide or potassium hydroxide, carbonates, such as sodium carbonate or potassium carbonate, or bicarbonates, such as potassium bicarbonate or sodium bicarbonate. In variant a, the compound of the formula III can itself serve as the base.

The end products can be isolated by concentration and or evaporation of the solvent, and can be purified by recrystallisation or trituration of the solid residue in solvents in which they are not readily soluble, such as ethers, aromatic hydrocarbons or chlorinated hydrocarbons.

The active substances of the formula I are stable compounds. Their handling requires no precautionary measures.

Surprisingly, it has been found that compounds of the formula I have a bactericidal spectrum against phytopathogenic bacteria which is very favourable for practical requirements. They have very advantageous curative. in some cases systemic and in particular preventive properties, and can be used for protecting numerous crop plants. The microorganisms which occur on plants or parts of plants (fruit, blossom, foliage, stem, tubers or roots) of various useful crops can be suppressed or destroyed with the active substances of the formula I, parts of plants which additionally grow later also remaining protected from such pests.

The active substances of the formula I and the compositions prepared therefrom are particularly effective against bacteria of the order Pseudomonadales, thus, for example, against bacteria of the family of Pseudomonadaceae, such as Pseudomonas and Xanthomonas species (*Pseudomonas tomato, Pseudomonas tabaci, Pseudomonas morsprunorum, Pseudomonas phaseolicola, Pseudomonas lachrymans, Xanthomonas campestris, Xanthomonas oryzae* and *Xanthomonas vesicatoria*).

The invention thus also relates to bactericidal compositions and the use of the compounds of the formula I for controlling phytopathogenic bacteria, in particular Xanthomonas species which damage plants, and preventive prophylaxis of an attack on plants.

The present invention furthermore also includes the preparation of agrochemical compositions which comprises intimate mixing of the active substance with one or more substances or groups of substances described in this application. The present invention also includes a method of treating plants which comprises application of the compounds of the formula I or of the novel compositions.

The following plant species are examples of target crops in the context of this invention for the fields of indication disclosed herein: cereals: (wheat, barley, rye, oats, rice, sorghum and related species); beet (sugarbeet and fodder beet); pomaceous fruit, stone fruit and berries: (apple, pear, plum, peach, almond, cherry, strawberry, raspberry and blackberry); pulse: (bean, lentil, pea, soya bean); oil crops: (rape, mustard, poppy, olive, sunflower, coconut, castor, cacao and groundnut); cucumber crops: (pumpkin, cucumber, melon); fibre crops: (cotton, flax, hemp and jute; citrus fruits: (orange, lemon, grapefruit and mandarin); vegetable varieties: (spinach, lettuce, asparagus, cabbage varieties, carrot, onion, tomato, potato and paprika); laurel crops: (avocado, cinnamon and camphor); or plants such as maize, tobacco, nut, coffee, sugar-cane, tea, vine, hop and banana and natural rubber crops, and ornamental plants (composites), preferably rice and paprika.

Active substances of the formula I are usually employed in the form of formulations and can be applied to the area or plant to be treated at the same time as or after other active substances. These other active substances can be fertilisers, carriers of trace elements or other products which influence plant growth. They can also be, however, selective herbicides, insecticides, fungicides, bactericides, nematicides, molluscicides or mixtures of several of these products, if necessary together with other carriers, surfactants or other application-promoting adjuvants conventionally used in the art of formulation.

Suitable carriers and adjuvants can be solid or liquid and correspond to the substances appropriate in the art of formulation, for example natural or regenerated mineral substances, solvents, dispersants, wetting agents, tackifiers, thickeners, binders or fertilisers.

A preferred method of application of an active substance of the formula I or of an agrochemical composition containing at least one of these active substances is application to the foliage (leaf application). The number of applications and the amount applied depend on the threat of attack by the corresponding pathogen (species of fungus). However, the active substances of the formula I can also enter the plants through the root via the soil (systemic action) by a method in which the location of the plant is soaked with a liquid formulation or the substances are incorporated into the soil in solid form, for example in the form of granules (soil application). The compounds of the formula I can, however, also be applied to seed (coating), by a method in which the seed is either soaked in a liquid formulation of the active substance or coated with a solid formulation. Moreover, other types of application are possible in particular cases, thus, for example, controlled treatment of the plant stems or the buds.

The compounds of the formula I are used here in unmodified form or, preferably, together with the assistants conventionally used in the art of formulation, and are thus processed in a known manner to, for example, emulsion concentrates, brushable pastes, directly sprayable or dilutable solutions, dilute emulsions, wettable powders, soluble powders, dusts or granules, by encapsulation in, for example, polymeric substances. The methods of application, such as spraying, misting, dusting, scattering, brushing or watering, are chosen according to the intended aims and the given circumstances, as is the type of composition. Favourable application amounts are generally 50 g to 5 kg of active substance (AS) per hectare; preferably 100 g to 2 kg/hectare, and in particular 200 g to 600 g of AS/hectare.

The formulations, i.e. the compositions, preparations or mixtures, containing the active substance of the formula I and, if appropriate, a solid or liquid adjuvant are prepared in a known manner, for example by intimate mixing and or grinding of the active substances with extenders, for example with solvents, solid carriers and, if necessary, surface-active compounds (surfactants).

Suitable solvents are: aromatic hydrocarbons, preferably $C_8$ to $C_{12}$ fractions, for example xylene mixtures or substituted naphthalenes, phthalic acid esters, such as dibutyl phthalate or dioctyl phthalate, aliphatic hydrocarbons, such as cyclohexane or paraffins, alcohols and glycols and ethers and esters thereof, such as ethanol, ethylene glycol, ethylene glycol monomethyl or monoethyl ether, ketones, such as cyclohexanone, strongly polar solvents, such as N-methyl-2-pyrrolidone, dimethylsulfoxide or dimethylformamide, and, where relevant, epoxidised vegetable oils, such as epoxidised coconut oil or soya bean oil; or water.

The solid carriers used, for example for dusts and dispersible powders, are as a rule ground natural minerals, such as calcite, talc, kaolin, montmorillonite or attapulgite. Highly disperse silica or highly disperse absorbent polymers may also be added to improve the physical properties. Suitable granular, adsorptive carriers for granules are porous types, for example pumice, broken brick, sepiolite or bentonite, and suitable non-adsorptive carriers are, for example, calcite or sand. A large number of pre-granulated materials of inorganic or organic nature, such as, in particular, dolomite or comminuted plant residues, can moreover be used. Further particularly advantageous adjuvants which promote application and can lead to a large reduction in the amount applied are natural (animal or vegetable) or synthetic phospholipids of the cephalin and lecithin series, for example phosphatidylethanolamine, phosphatidylserine, phosphatidylcholine, sphingomyelin, phosphatidylinositol, phosphatidylglycerol, lysolecithin, plasmalogens or cardiolipin, which can be isolated, for example, from animal or vegetable cells, in particular from the brain, heart, lung or liver or from egg yolks or soya bean. Examples of commercial mixtures which can be used are phosphatidylcholine mixtures. Examples of synthetic phospholipids are dioctanoylphosphatidylcholine and dipalmitoylphosphatidylcholine.

Suitable surface-active compounds, depending on the nature of the active substance of the formula I to be formulated, are non-ionic, cationic and/or anionic surfactants with good emulsifying, dispersing and wetting properties. Surfactants are also to be understood as meaning surfactant mixtures.

Suitable anionic surfactants can be either so-called water-soluble soaps or water-soluble synthetic surface-active compounds.

Soaps are the alkali metal, alkaline earth metal or unsubstituted or substituted ammonium salts of higher fatty acids ($C_{10}$–$C_{22}$), for example the Na or K salts of oleic acid or stearic acid, or of naturally occurring fatty acid mixtures, which can be obtained, for example, from coconut oil or tallow oil. The fatty acid methyl-laurin salts are also suitable.

However, so-called synthetic surfactants, in particular fatty sulfonates, fatty sulfates, sulfonated benzimidazole derivatives or alkylsulfonates, are more frequently used.

The fatty sulfonates or sulfates are as a rule in the form of alkali metal, alkaline earth metal or unsubstituted or substituted ammonium salts and contain an alkyl radical having 8 to 22C atoms, alkyl also including the alkyl moiety of acyl radicals, for example the Na or Ca salt of ligninsulfonic acid, dodecylsulfuric acid ester or a fatty alcohol sulfate mixture prepared from naturally occurring fatty acids. These compounds also include the salts of sulfuric acid esters and sulfonic acids of fatty alcohol/ethylene oxide adducts. The sulfonated benzimidazole derivatives preferably contain 2-sulfonic acid groups and a fatty acid radical having 8–22C atoms. Examples of alkylarylsulfonates are the Na, Ca or triethanolamine salts of dodecylbenzenesulfonic acid, dibutylnaphthalenesulfonic acid or a naphthalenesulfonic acid/formaldehyde condensate.

Corresponding phosphates, for example salts of the phosphoric acid ester of a p-nonylphenol-(4–14)-ethylene oxide adduct, are also suitable.

Particularly suitable non-ionic surfactants are polyglycol ether derivatives of aliphatic or cycloaliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical of the alkylphenols.

Other suitable non-ionic surfactants are the water-soluble adducts, containing 20 to 250 ethylene glycol ether groups and 10 to 100 g propylene glycol ether groups, of polyethylene oxide and polypropylene glycol, ethylenediaminopolypropylene glycol and an alkylpolypropylene glycol having 1 to 10 carbon atoms in the alkyl chain. The compounds mentioned usually contain 1 to 5 ethylene glycol units per propylene glycol unit.

Examples of non-ionic surfactants are nonylphenolpolyethoxyethanols, castor oil polyglycol ethers, polypropylene polyethylene oxide adducts, tributylphenoxypolyethyleneethanol, polyethylene glycol and octylphenoxypolyethoxyethanol.

Fatty acid esters of polyoxyethylene sorbitan, such as polyoxyethylene sorbitan trioleate, are also suitable.

The cationic surfactants are, in particular, quaternary ammonium salts which contain at least one alkyl radical having 8 to 22C atoms as an N-substituent and lower alkyl or benzyl radicals, which may or may not be halogenated, or lower hydroxyalkyl radicals, as further substituents. The salts are preferably in the form of halides, methylsulfates or ethylsulfates, and are, for example, stearyltrimethylammonium chloride or benzyldi(2-chloroethyl)ethylammonium bromide.

The surfactants conventionally used in the art of formulation are described, inter alia, in the following publications:

"Mc Cutcheon's Detergents and Emulsifiers Annual" BC Publishing Corp., Ridgewood, N.J., 1981 and Helmut Stache "Tensid Taschenbuch" (Surfactant Handbook"), Carl Hanser-Verlag Munich/Vienna 1981.

The agrochemical formulations as a rule contain 0.1 to 99%, in particular 0.1 to 95%, of active substance of the formula I, 99.9 to 1%, in particular 99.8 to 5%, of a solid or liquid adjuvant and 0 to 25%, in particular 0.1 to 25%, of a surfactant.

Whilst concentrated compositions are rather preferred as commercial products, the final user as a rule employs dilute compositions.

The compositions can also contain other adjuvants, such as stabilisers, antifoams, viscosity regulators, binders, tackifiers and fertilisers, or other active substances, in order to achieve special effects.

Such agrochemical compositions are a component of the present invention.

The examples which follow serve to further illustrate the invention, without restricting it.

PREPARATION EXAMPLES

Example H1

Preparation of

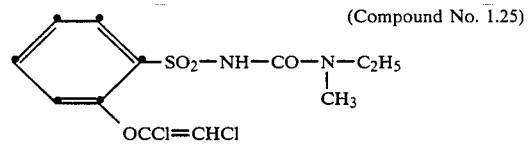

(Compound No. 1.25)

N-[2-(1,2-Dichlorovinyloxy)phenylsulfonyl]-N'-methyl-N'-ethylurea

A solution of 2.1 g of N-methylethylamine in 50 ml of absolute dioxane is added dropwise to a solution of 10.3 g of 2-(1,2-dichlorovinyloxy)phenyl isocyanate in 100 ml of absolute dioxane at 20° to 25° C., and stirring of the mixture is continued at room temperature for 15 hours. The reaction solution is then evaporated and the residue is brought to crystallisation by addition of a mixture of acetone/hexane. The product is filtered off and dried. Yield: 7.5 g. Melting point: 179°–180° C.

Example H2

Preparation of

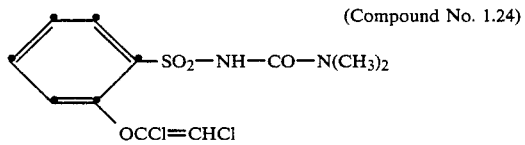

(Compound No. 1.24)

N-[2-(1,2-Dichlorovinyloxy)phenylsulfonyl]-N',N'-dimethylurea

A solution of 10.2 g of dimethylcarbamyl chloride in 10 ml of methylene chloride is added dropwise to a mixture of 10.7 g of 2-(1,2-dichlorovinyloxy)phenylsulfonamide, 12.2 g of 1,8-diazabicyclo[5.4.0]undec-7-ene in 100 ml of methylene chloride at 20° to 25° C. and the mixture is refluxed for 2 hours. The solvent is then evaporated off and the residue is dissolved in 5% sodium carbonate solution. The solution is filtered and acidified with 10% hydrochloric acid, whereupon the product precipitates as crystals. After filtration and drying, 12.1 g of N-[2-(1,2-dichlorovinyloxy)phenylsulfonyl]-N',N'-dimethylurea are obtained. Melting point: 218°–220° C.

Example H3

Preparation of

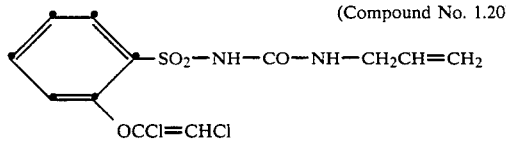

(Compound No. 1.20)

N-[2-(1,2-Dichlorovinyloxy)phenylsulfonyl]-N'-allylurea

A solution of 3.3. g of allyl isocyanate in 10 ml of methylene chloride is added dropwise to a mixture of 10.7 g of 2-(1,2-dichlorovinyloxy)phenylsulfonamide and 6.1 g of 1,8-diazabicyclo[5.4.0]undec-7-ene in 100 ml of methylene chloride, with stirring. When the exothermic reaction has subsided, stirring of the reaction mixture is continued at 20° to 25° C. for a further hour and the solvent is then evaporated off. The residue is dissolved in 5% sodium carbonate solution. The solution is filtered and acidified with 10% hydrochloric acid, whereupon the product precipitates as crystals. After filtration and drying, 13.2 g of N-[2-(1,2-dichlorovinyloxy)phenylsulfonyl]-N'-allylurea are obtained. Melting point: 187°–188° C.

Example H4

Preparation of

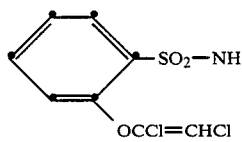

(Compound No. 2.2)

SO$_2$—NH—CS—NH—CH$_3$

N-[2-(1,2-Dichlorovinyloxy)phenylsulfonyl]-N'-methylthiourea 13.4 g of 2-(1,2-dichlorovinyloxy)phenylsulfonamide and 3.65 g of methyl isothiocyanate are dissolved in 50 ml of acetonitrile, and 7.8 g of 1,8-diazabicyclo[5.4.0]undec-7-ene are added with cooling (0° to 5° C.) and stirring. The resulting red reaction solution is left to stand for 24 hours, 4.8 g of methanesulfonic acid are then added and the mixture is diluted with water to a volume of 1 liter. The crystals which separate out are filtered off, washed with methanol and dried. Yield: 15 g. Melting point: 185°–187° (decomposition).

Example H5

Preparation of

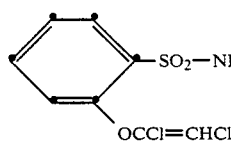

(Compound No. 1.2)

SO$_2$—NH—CO—NH—CH$_3$

N-[2-(1,2-Dichlorovinyloxy)phenylsulfonyl]-N'-methylurea 1.9 g of methyl isocyanate are added to a suspension of 6.7 g of 2-(1,2-dichlorovinyloxy)phenylsulfonamide in 50 ml of methylene chloride. 3.3 g of triethylamine are added dropwise to this mixture at 20° to 25° C. in the course of 10 minutes, a clear solution being formed. Stirring of this solution is continued for a further hour, and the solution is then evaporated to dryness. The residue is dissolved in 5% aqueous sodium carbonate solution and acidified with 10% hydrochloric acid, whereupon the product precipitates as crystals. After filtration and drying, 7.8 g of N-[2-(1,2-dichlorovinyloxy)phenylsulfonyl]-N'-methylurea are obtained. Melting point: 228°–229° C.

The compounds of the formula I listed below are also prepared by procedures analogous to those described:

TABLE 1

Compounds of the formula

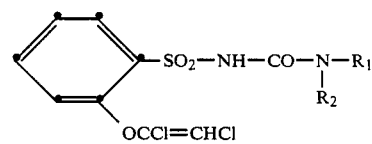

| Compound No. | R$_1$ | R$_2$ | Physical constant (0° C.) |
|---|---|---|---|
| 1.1 | H | H | Melting point 219–221° |
| 1.2 | H | CH$_3$ | Melting point 228–229° |
| 1.3 | H | C$_2$H$_5$ | |
| 1.4 | H | C$_3$H$_7$—n | |
| 1.5 | H | C$_3$H$_7$—i | Melting point 156–160° |
| 1.6 | H | C$_4$H$_9$—n | Melting point 123–126° |
| 1.7 | H | C$_4$H$_9$—s | |
| 1.8 | H | C$_4$H$_9$—t | |
| 1.9 | H | C$_5$H$_{11}$—n | |
| 1.10 | H | C$_2$H$_4$C(CH$_3$)HCH$_3$ | |
| 1.11 | H | C$_6$H$_{13}$—n | |
| 1.12 | H | C$_2$H$_4$C(CH$_3$)$_3$ | |
| 1.13 | H | OCH$_3$ | Melting point 154–156° |
| 1.14 | H | OC$_2$H$_5$ | |
| 1.15 | H | OC$_3$H$_7$—i | |
| 1.16 | H | OC$_3$H$_7$—n | |
| 1.17 | H | OC$_4$H$_9$—n | |
| 1.18 | H | OC$_5$H$_{11}$—n | |
| 1.19 | H | OC$_6$H$_{13}$—n | |
| 1.20 | H | CH$_2$CH=CH$_2$ | Melting point 187–188° |
| 1.21 | H | CH$_2$C≡CH | |
| 1.22 | H | C(CH$_3$)$_2$C≡CH | Melting point 153–156° |
| 1.23 | H | CH$_2$CH$_2$CH=CH$_2$ | |
| 1.24 | CH$_3$ | CH$_3$ | Melting point 218–220° |
| 1.25 | CH$_3$ | C$_2$H$_5$ | Melting point 179–180° |
| 1.26 | CH$_3$ | C$_3$H$_7$—n | |
| 1.27 | CH$_3$ | C$_3$H$_7$—i | |
| 1.28 | C$_2$H$_5$ | C$_2$H$_5$ | |
| 1.29 | CH$_3$ | OCH$_3$ | Melting point 154–156° |
| 1.30 | CH$_3$ | OC$_2$H$_5$ | |
| 1.31 | CH$_3$ | OC$_3$H$_7$—n | |
| 1.32 | CH$_3$ | CH$_2$CH=CH$_2$ | Melting point 144–146° |
| 1.33 | CH$_3$ | CH$_2$CH$_2$CH=CH$_2$ | |
| 1.34 | CH$_2$CH=CH$_2$ | CH$_2$CH=CH$_2$ | |
| 1.35 | C$_2$H$_5$ | CH$_2$CH=CH$_2$ | |
| 1.36 | C$_3$H$_7$—n | CH$_2$CH=CH$_2$ | Resin |
| 1.37 | C$_2$H$_5$ | CH$_2$C(CH$_3$)=CH$_2$ | |
| 1.38 | C$_3$H$_7$—i | CH$_2$C(CH$_3$)=CH$_2$ | Resin |
| 1.39 | CH$_3$ | CH$_2$C(CH$_3$)=CH$_2$ | |
| 1.40 | H | CH$_2$C(CH$_3$)=CH$_2$ | |
| 1.41 | CH$_3$ | CH$_2$C≡CH | Semi-crystalline |
| 1.42 | CH$_3$ | C(CH$_3$)$_2$C≡CH | |

TABLE 2

Compounds of the formula

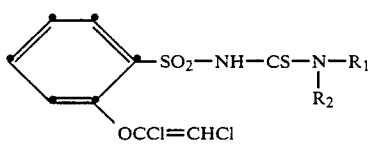

| Compound No. | $R_1$ | $R_2$ | Physical constant (0° C.) |
|---|---|---|---|
| 2.1 | H | H | |
| 2.2 | H | $CH_3$ | Melting point 185–187° |
| 2.3 | H | $C_2H_5$ | |
| 2.4 | H | $C_3H_7$—n | |
| 2.5 | H | $C_3H_7$—i | Melting point 146–148° |
| 2.6 | H | $C_4H_9$—n | |
| 2.7 | H | $C_4H_9$—s | |
| 2.8 | H | $C_4H_9$—t | |
| 2.9 | H | $C_5H_{11}$—n | |
| 2.10 | H | $C_2H_4C(CH_3)HCH_3$ | |
| 2.11 | H | $C_6H_{13}$—n | |
| 2.12 | H | $C_2H_4C(CH_3)_3$ | |
| 2.13 | H | $OCH_3$ | Viscous oil |
| 2.14 | H | $OC_2H_5$ | Semi-crystalline |
| 2.15 | H | $OC_3H_7$—i | |
| 2.16 | H | $OC_3H_7$—n | |
| 2.17 | H | $OC_4H_9$—n | |
| 2.18 | H | $OC_5H_{11}$—n | |
| 2.19 | H | $OC_6H_{13}$—n | |
| 2.20 | H | $CH_2CH=CH_2$ | Melting point 129–131° |
| 2.21 | H | $CH_2C\equiv CH$ | |
| 2.22 | H | $C(CH_3)_2C\equiv CH$ | |
| 2.23 | H | $CH_2CH_2CH=CH_2$ | |
| 2.24 | $CH_3$ | $CH_3$ | Resin |
| 2.25 | $CH_3$ | $C_2H_5$ | |
| 2.26 | $CH_3$ | $C_3H_7$—n | |
| 2.27 | $CH_3$ | $C_3H_7$—i | Resin |
| 2.28 | $C_2H_5$ | $C_2H_5$ | |
| 2.29 | $CH_3$ | $OCH_3$ | |
| 2.30 | $CH_3$ | $OC_2H_5$ | |
| 2.31 | $CH_3$ | $OC_3H_7$—n | |
| 2.32 | $CH_3$ | $CH_2CH=CH_2$ | |
| 2.33 | $CH_3$ | $CH_2CH_2CH=CH_2$ | |
| 2.34 | $CH_2CH=CH_2$ | $CH_2CH=CH_2$ | |
| 2.35 | $C_2H_5$ | $CH_2CH=CH_2$ | |
| 2.36 | $C_3H_7$—n | $CH_2CH=CH_2$ | |
| 2.37 | $C_2H_5$ | $CH_2C(CH_3)=CH_2$ | |
| 2.38 | $C_3H_7$—i | $CH_2C(CH_3)=CH_2$ | |
| 2.39 | $CH_3$ | $CH_2C(CH_3)=CH_2$ | |
| 2.40 | H | $CH_2C(CH_3)=CH_2$ | |
| 2.41 | $CH_3$ | $CH_2C\equiv CH$ | |
| 2.42 | $CH_3$ | $C(CH_3)_2C\equiv CH$ | |

FORMULATION EXAMPLES FOR LIQUID ACTIVE SUBSTANCES OF THE FORMULA I
(%=PERCENT BY WEIGHT)

| F1. Emulsion concentrates | a | b | c |
|---|---|---|---|
| Active substance from the tables | 25% | 40% | 50% |
| Ca Dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from such concentrates by dilution with water.

| F2. Solutions | a | b | c | d |
|---|---|---|---|---|
| Active substance from the tables | 80% | 10% | 5% | 95% |
| Ethylene glycol monomethyl ether | 20% | — | — | — |
| Polyethylene glycol MW 400 | — | 70% | — | — |
| N—Methyl-2-pyrrolidone | — | 20% | — | — |
| Epoxidised coconut oil | — | — | 1% | 5% |
| Benzine (boiling range 160–190° C.) | — | — | 94% | — |

(MW = molecular weight)

The solutions are suitable for application in the form of very small drops.

| F3. Granules | a | b |
|---|---|---|
| Active substance from the table | 5% | 10% |
| Kaolin | 94% | — |
| Highly disperse silica | 1% | — |
| Attapulgite | — | 90% | p The active substance is dissolved in methylene chloride, the solution is sprayed onto the carrier and the solvent is then evaporated off in vacuo.

| F4. Dusts | a | b |
|---|---|---|
| Active substance from the tables | 2% | 5% |
| Highly disperse silica | 1% | 5% |
| Talc | 97% | — |
| Kaolin | — | 90% |

Ready-to-use dusts are obtained by intimate mixing of the carriers with the active substance.

FORMULATION EXAMPLES FOR SOLID ACTIVE SUBSTANCES OF THE FORMULA I
(%=PERCENT BY WEIGHT)

| F5. Wettable powders | a | b | c |
|---|---|---|---|
| Active substance from the tables | 25% | 50% | 75% |
| Na Ligninsulfonate | 5% | 5% | — |
| Na Laurylsulfate | 3% | — | 5% |
| Na Diisobutylnaphthalenesulfonate | — | 6% | 10% |
| Octylphenol polyethylene glycol ether (7–8 mol of ethylene oxide) | — | 2% | — |
| Highly disperse silica | 5% | 10% | 10% |
| Kaolin | 62% | 27% | — |

The active substance is mixed thoroughly with the adjuvants and the mixture is ground thoroughly in a suitable mill. Wettable powders are obtained, which can be diluted with water to give suspensions of any desired concentration.

| F6. Emulsion concentrate | |
|---|---|
| Active substance from the tables | 10% |
| Octylphenol polyethylene glycol ether (4–5 mol of ethylene oxide) | 3% |
| Ca Dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by dilution with water.

| F7. Dusts | a | b |
|---|---|---|
| Active substance from the tables | 5% | 8% |

-continued

| F7. Dusts | a | b |
|---|---|---|
| Talc | 95% | — |
| Kaolin | — | 92% |

Ready-to-use dusts are obtained by mixing the active substance with the carrier and grinding the mixture on a suitable mill.

| F8. Extruded granules | |
|---|---|
| Active substance from the tables | 10% |
| Na Ligninsulfonate | 2% |
| Carboxymethylcellulose | 1% |
| Kaolin | 87% |

The active substance is mixed with the adjuvants and the mixture is ground and moistened with water. This mixture is extruded and subsequently dried in a stream of air.

| F9. Coated granules | |
|---|---|
| Active substance from the tables | 3% |
| Polyethylene glycol (MW 200) | 3% |
| Kaolin | 94% |

(MW = molecular weight)

The finely ground active substance is uniformly applied, in a mixer, to the kaolin, which has been moistened with polyethylene glycol. Dust-free coated granules are obtained in this manner.

| F10. Suspension concentrate | |
|---|---|
| Active substance from the tables | 40% |
| Ethylene glycol | 10% |
| Nonylphenol polyethylene glycol ether (15 mol of ethylene oxide) | 6% |
| Na Ligninsulfonate | 10% |
| Carboxymethylcellulose | 1% |
| 37% Aqueous formaldehyde solution | 0.2% |
| Silicone oil in the form of a 65% aqueous emulsion | 0.8% |
| Water | 32% |

The finely ground active substance is intimately mixed with the adjuvants. A suspension concentrate is thus obtained, from which suspensions of any desired concentration can be prepared by dilution with water.

BIOLOGICAL EXAMPLES

Example B1

Action against *Xanthomonas oryzae* on rice (a) Residual-protective action

After being grown in a greenhouse for 3 weeks, rice plants of the variety "Caloro" or "S6" were sprayed with the test substance in the form of a spray liquor (0.06% of active substance). After this spray coating had dried for one day, the plants were placed in a climatically controlled chamber at 24° C. and 75–85% relative atmospheric humidity and were infected. Infection was effected by cutting off the tips of leaves with scissors which had first been immersed in a suspension of *Xanthomonas oryzae.* After incubation in the same room for 10 days, the cut leaves withered, curled up and became necrotic. The extent of these disease symptoms was used to evaluate the residual activity of the test substance.

(b) Systemic action

After being grown in a greenhouse for 3 weeks, rice plants of the variety "Caloro" or "S6" were watered with a suspension of the test substance (0.006% of active substance, based on the soil volume). Three days after this treatment, the plants were placed in a climatically controlled chamber at 24° C. and 75–85% relative atmospheric humidity and were infected. Infection was effected by cutting off the tips of leaves with scissors which had first been immersed in a suspension of *Xanthomonas oryzae.* After incubation in the same room for 10 days, the cut leaves wilted, curled up and became necrotic. The extent of these disease symptoms was used to evaluate the systemic activity of the test substance.

Compounds from the tables showed a good action against Xanthomonas bacteria, i.e. compounds Nos. 1.1, 1.2, 1.5, 1.6, 1.13, 1.20, 1.22, 1.24, 1.25, 1.32, 2.2, 1.29, 2.5 and 2.20, inter alia, almost completely inhibited (0 to 5%) the occurrence of necrotic spots in the residual-protective and sytemic treatment of rice. Compounds 1.2 and 1.25 also completely prevented (0%) the fungal attack at even lower application amounts. Untreated but infected rice plants (controls) exhibited 100% necrosis.

Example B2

Action against *Xanthomonas vesicatoria* on paprika (a) Residuäl-protective action After being grown in a greenhouse for 3 weeks, paprika plants of the variety "California Wonder" were sprayed the test substance in the form of a spray liquor (0.06% of active substance). After this spray coating had dried on for one day, the plants were placed in a climatically controlled chamber at 26° C. and 95–100% relative atmospheric humidity and were infected by spraying the undersides of the leaves with a standardised suspension of *Xanthomonas vesicatoria.* After incubation in the same room for 6 days, round, initially aqueous and later necrotic, spots lighter in colour developed on the leaves. The extent of these spots was used to evaluate the residual activity of the test substance.

(b) Systemic action

After being grown in a greenhouse for 3 days, paprika plants of the variety "California Wonder" were watered with a suspension of the test substance (0.006% of active substance based on the soil volume). Three days after this treatment, the plants were placed in a climatically controlled chamber at 26° C. and a 95–100% relative atmospheric humidity, and were infected by spraying the undersides of the leaves with a standardised suspension of *Xanthomonas vesicatoria.* After incubation in the same room for 6 days, round, initially aqueus and later necrotic spots lighter in colour developed on the leaves. The extent of these spots was used to evaluate the systemic activity of the test substance. Compounds from both tables almost completely prevented the occurrence of spots.

The substances mentioned in Example B1 almost completely inhibited (0 to 5%) the occurrence of necroses in both experiments. Control: 100%.

Example B3

Action against *Pseudomonas tomato* on tomatoes (a) Residual-protective action

After being grown in a greenhouse for 3 weeks, tomato plants of the variety Rentita were sprayed with the test substance in the form of a spray liquor (0.06% of active substance). After this spray coating had dried on for one day, the plants were placed in a climatically controlled chamber at 22° C. and 95–100% relative atmospheric humidity and were infected by spraying the undersides of the leaves with a standardised suspension of *Pseudomonas tomato*. After incubation in the same room for 8 days, small black spots with yellow areola developed on the leaves. The average number of spots per leaf was used as the basis for evaluating the activity of the test substance.

(b) Systemic action

After being grown in a greenhouse for 3 weeks, tomato plants of the Rentita variety were watered with a suspension of the test substance (0.006% of active substance, based on the soil volume). Three days after this treatment, the plants were placed in a climatically controlled chamber at 22° C. and 95–100% relative atmospheric humidity and were infected by spraying the undersides of the leaves with a standardised suspension of *Pseudomonas tomato*. After incubation in the same room for 8 days, small black spots with yellow areolas developed on the leaves. The average number of such spots per leaf was used as a basis for evaluating the activity of the test substance.

The substances mentioned in Example B1 almost completely inhibited (0 to 5%) the occurrence of leaf necroses in both tests. Control: 100%.

What is claimed is:

1. A compound of the formula

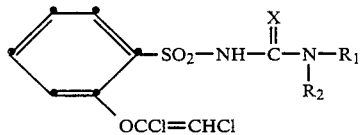

in which X is oxygen or sulfur; $R_1$ is hydrogen, $C_1$–$C_{12}$-alkyl, $C_2$–$C_6$-alkenyl or $C_2$–$C_6$-alkynyl; and $R_2$ is hydrogen, $C_1$–$C_{12}$-alkyl, $C_2$–$C_6$-alkenyl, $C_2$–$C_6$-alkynyl or $C_1$–$C_6$-alkoxy; and the salts of this compound.

2. A compound of claim 1, in which $R_1$ is hydrogen or $C_1$–$C_6$-alkyl; and $R_2$ is hydrogen, $C_1$–$C_6$-alkyl, $C_2$–$C_6$-alkenyl, $C_2$–$C_6$-alkynyl or $C_1$–$C_6$-alkoxy.

3. A compound of claim 2, in which $R_1$ is hydrogen or $C_1$–$C_3$-alkyl; and $R_2$ is $C_1$–$C_6$-alkyl or $C_1$–$C_6$-alkoxy.

4. A compound of claim 3, in which X is oxygen; and $R_2$ is $C_1$–$C_6$-alkyl.

5. A compound of claim 2, in which $R_1$ is hydrogen or $C_1$–$C_3$-alkyl; and $R_2$ is $C_2$–$C_6$-alkenyl or $C_2$–$C_6$-alkynyl.

6. A compound of claim 5, in which X is oxygen; and $R_2$ is $C_2$–$C_4$-alkenyl or $C_2$–$C_4$-alkynyl.

7. A compound of claim 1, in which X is oxygen and $R_1$ and $R_2$ independently of one another are hydrogen, $C_2$–$C_6$-alkenyl or $C_2$–$C_6$-alkynyl.

8. A compound of claim 2, selected from the series consisting of
N-[2-(1,2-dichlorovinyloxy)phenylsulfonyl]-urea; N-[2-(1,2-dichlorovinyloxy)phenylsulfonyl]-N'-methylurea; N-[2-(1,2-dichlorovinyloxy)phenylsulfonyl]-N'-isopropylurea; N-[2-(1,2-dichlorovinyloxy)phenylsulfonyl]-N'-n-butyurea; N-[2-(1,2-dichlorovinyloxy)phenylsulfonyl]-N'-methoxy-N'-methylurea; N-[2-(1,2-dichlorovinyloxy)phenylsulfonyl]-N'-allylurea; N-[2-(1,2-dichlorovinyloxy)phenylsulfonyl]-N',N'-dimethylurea (compound No. 1.24); N-[2-(1,2-dichlorovinyloxy)phenylsulfonyl]-N'-methyl-N'-ethylurea; N-[2-(1,2-dichlorovinyloxy)phenylsulfonyl]-N'-methyl-N'-allylurea; N-[2-(1,2-dichlorovinyloxy)phenylsulfonyl]-N'-methylthiourea; N-[2-(1,2-dichlorovinyloxy)phenylsulfonyl]-N'-isopropylthiourea and N-[2-(1,2-dichlorovinyloxy)phenylsulfonyl]-N'-allylthiourea.

9. Bactericidal composition which contains, in addition to an agriculturally suitable carrier and formulation assistant, a compound of the formula

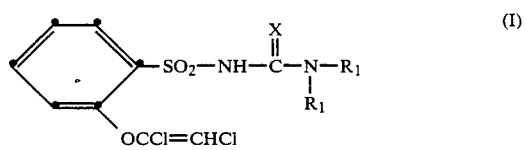

in which X is oxygen or sulfur, $R_1$ is hydrogen, $C_1$–$C_{12}$-alkyl, $C_2$–$C_6$-alkenyl or $C_2$–$C_6$-alkynyl; and $R_2$ is hydrogen, $C_1$–$C_{12}$-alkyl, $C_2$–$C_6$-alkenyl, $C_2$–$C_6$-alkynyl or $C_1$–$C_6$-alkoxy; or a salt of this compound, as at least one active component.

10. A method of combating phytopathogenic bacteria, which comprises applying a bactericidally active amount of a compound of the formula

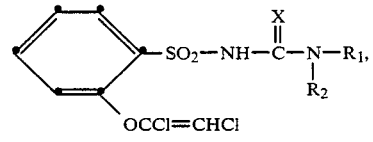

in which X is oxygen or sulfur, $R_1$ is hydrogen, $C_1$–$C_{12}$-alkyl, $C_2$–$C_6$-alkenyl or $C_2$–$C_6$-alkynyl; and $R_2$ is hydrogen, $C_1$–$C_{12}$-alkyl, $C_2$–$C_6$-alkenyl, $C_2$–$C_6$-alkynyl or $C_1$–$C_6$-alkoxy; or a salt of this compound, to the plants or their location.

* * * * *